(12) United States Patent
Place et al.

(10) Patent No.: US 6,469,016 B1
(45) Date of Patent: Oct. 22, 2002

(54) TREATMENT OF FEMALE SEXUAL DYSFUNCTION USING PHOSPHODIESTERASE INHIBITORS

(75) Inventors: Virgil A. Place, Kawaihae, HI (US); Leland F. Wilson, Menlo Park, CA (US); Paul C. Doherty, Jr., Cupertino, CA (US); Mark S. Hanamoto, Belmont, CA (US); Alfred P. Spivack, Menlo Park, CA (US); Neil Gesundheit, Los Altos, CA (US); Sean R. Bennett, Denver, CO (US)

(73) Assignee: Vivus, Inc., Mountain View, CA (US)

( * ) Notice: Subject to any disclaimer, the term of this patent is extended or adjusted under 35 U.S.C. 154(b) by 0 days.

(21) Appl. No.: 09/499,959

(22) Filed: Feb. 8, 2000

Related U.S. Application Data

(60) Division of application No. 09/181,316, filed on Oct. 27, 1998, now abandoned, which is a continuation-in-part of application No. 08/959,064, filed on Oct. 28, 1997, now Pat. No. 5,877,216, and a continuation-in-part of application No. 08/959,057, filed on Oct. 28, 1997, now abandoned.

(51) Int. Cl.$^7$ .................. A61K 31/51; A61K 31/44
(52) U.S. Cl. .................. 514/262; 514/261; 514/341
(58) Field of Search ............... 514/341, 261, 514/262

(56) References Cited

U.S. PATENT DOCUMENTS

| | | |
|---|---|---|
| 3,800,038 A | 3/1974 | Rudel |
| 3,948,254 A | 4/1976 | Zaffaroni |
| 3,967,618 A | 7/1976 | Zaffaroni |
| 4,014,987 A | 3/1977 | Heller et al. |
| 4,112,942 A | 9/1978 | Scaife |
| 4,128,577 A | 12/1978 | Nelson |
| 4,254,145 A | 3/1981 | Birnbaum |
| 4,454,339 A | 6/1984 | Skuballa |
| 4,507,323 A | 3/1985 | Stern |
| 4,521,421 A | 6/1985 | Foreman |
| 4,564,362 A | 1/1986 | Burnhill |
| 4,680,312 A | 7/1987 | Johnson |
| 4,818,517 A | 4/1989 | Kwee et al. |
| 4,961,931 A | 10/1990 | Wong |
| 4,976,692 A | 12/1990 | Atad |
| 5,190,967 A | 3/1993 | Riley |
| 5,565,466 A | 10/1996 | Giocco et al. |
| 5,698,589 A | 12/1997 | Allen |
| 5,731,339 A | 3/1998 | Lowrey |
| 5,773,020 A | 6/1998 | Place |
| 5,773,457 A | 6/1998 | Nahoum |
| 5,891,915 A | 4/1999 | Wysor et al. |
| 5,958,926 A * | 9/1999 | Garvey et al. ............... 514/253 |
| 6,031,002 A | 2/2000 | Wysor et al. |
| 6,107,331 A * | 8/2000 | MacLean et al. ............ 514/428 |
| 6,150,400 A * | 11/2000 | Nyirjesy et al. ............. 514/456 |

FOREIGN PATENT DOCUMENTS

| | | |
|---|---|---|
| WO | WO 94/28902 | 12/1994 |
| WO | WO 96/16644 | 6/1996 |
| WO | WO 99/20266 | 4/1999 |

OTHER PUBLICATIONS

U.S. patent application Ser. No. 08/954,122, Neal, filed Oct. 27, 1997.
U.S. patent application Ser. No. 09/391,412, Neal, filed Sep. 8, 1999.
Frishman et al. (1992), "Evaluation of Astroglide, a New Vaginal Lubricant: Effects of Lenght of Exposure and Concentration on Sperm Motility," *Fertility and Sterility* 58(3):630.
Levin (1991), "VIP, Vagina, Clitoral and Periurethral Glans—An Update on Human Femal Genital Arousal," *Exp. Clin. Endocrinol.* 98(2):61–69.
Semmens, (1974)*Medical Aspects of Human Sexuality* 8:85–86.

* cited by examiner

*Primary Examiner*—Theodore J. Criares
(74) *Attorney, Agent, or Firm*—Reed & Associates; Diane E. Reed (57) ABSTRACT

Methods and formulations for treating female sexual dysfunction are provided. A pharmaceutical composition formulated so as to contain a selected vasoactive agent is administered to the vagina, vulvar area or urethra of the individual undergoing treatment. Suitable vasoactive agents are vasodilators, including naturally occurring prostaglandins, synthetic prostaglandin derivatives, endothelial-derived relaxation factors, vasoactive intestinal polypeptide agonists, smooth muscle relaxants, leukotriene inhibitors, and others. The formulations are also useful for preventing the occurrence of yeast infections, improving vaginal muscle tone and tissue health, enhancing vaginal lubrication, and minimizing excess collagen deposition. A clitoral drug delivery device is also provided.

64 Claims, 1 Drawing Sheet

TREATMENT OF FEMALE SEXUAL DYSFUNCTION USING PHOSPHODIESTERASE INHIBITORS

CROSS-REFERENCE TO RELATED APPLICATIONS

This is a divisional of U.S. Ser. No. 09/181,316, filed Oct. 27, 1998, now abandoned, which was a continuation-in-part of U.S. Ser. No. 08/959,064, filed Oct. 28, 1997, now U.S. Pat. No. 5,877,216, and of U.S. patent application Ser. No. 08/959,057, also filed Oct. 28, 1997, abandoned, the disclosures of which are hereby incorporated by reference.

TECHNICAL FIELD

This invention relates generally to methods and pharmaceutical formulations for treating female sexual dysfunction, and more particularly relates to vaginal, vulvar and/or urethral administration of a vasoactive agent, such as a prostaglandin, in such treatment. The invention further relates to additional methods of using the present pharmaceutical formulations, including, but not limited to, the prevention of yeast infections and the improvement of vaginal muscle tone.

BACKGROUND

Sexual response in women is generally classified into four stages: excitement, plateau, orgasm, and resolution. Masters and Johnson, *Human Sexual Response* (Boston, Mass.: Little, Brown & Co., 1966). With sexual arousal and excitement, vasocongestion and muscular tension increase progressively, primarily in the genitals, and is manifested by increased blood flow, elevated luminal oxygen tension, and vaginal surface lubrication as a result of plasma transudation that saturates the fluid reabsorptive capacity of the vaginal epithelium. Vasoactive intestinal polypeptide ("VIP") release may induce the physiological changes of sexual arousal and excitement, and may be the major neurotransmitter that participates in the innervation of the vaginal blood supply. Peptide histidine methionine has been co-located with VIP within nerve fibers that innervate small blood vessels, smooth muscle and epithelial cells in the vaginal tract.

Sexual excitement is initiated by any of a number of psychogenic or somatogenic stimuli and must be reinforced to result in orgasm. With continued stimulation, excitement progresses in intensity into a plateau stage, from which the individual can shift into orgasm. The orgasmic stage is characterized by a rapid release from vasocongestion and muscular tension.

During the various stages of sexual response, characteristic genital and extragenital responses occur. Estrogens magnify the sexual responses; however, sexual responses may also occur in estrogen-deficient individuals. Sexual dysfunction may be due to organic or functional disturbances. For example, a variety of diseases affecting neurologic function, including diabetes mellitus and multiple sclerosis, may interrupt sexual arousal. More commonly, local pelvic disorders, such as endometriosis and vaginitis, both of which cause dyspareunia (difficult or painful coitus) may also affect a woman's sexual response. In addition, estrogen deficiency, causing vaginal atrophy and dyspareunia, is a common cause of sexual dysfunction. For a discussion of other causes of female sexual dysfunction, see, e.g., Kaplan, *The Evaluation of Sexual Disorders: Psychological and Medical Aspects* (New York: Brunner-Mazel, 1983), and Kolodny et al., *Textbook of Sexual Medicine* (Boston, Mass.: Little, Brown & Co., 1979).

Excitement stage dysfunction generally involves touch sensation impairment, loss of clitoral sensation, vaginal dryness and urinary incontinence. Such excitement phase dysfunction generally results in dyspareunia. Dyspareunia is thought to affect approximately 40% of women, due in large part to inadequate lubrication. It has been estimated that over 40 million women will suffer dyspareunia at some time in their lives. On the order of twenty-five million will experience dyspareunia in the peri- and postmenopausal period (see Kelly, S. (1992) *Clinical Practice and Sexuality* 8(8):2 and Sato et al. (1992) *Clinical Practices in Sexuality* 8(5):1). Contemporary symptomatic treatments generally involve the use of physiologically safe lubricants such as egg white, K-Y surgical lubrication jelly (hydroxyethyl-cellulose), Astroglide®, and Replens®. See, for example, Semmens (1974) *Medical Aspects of Human Sexuality* 8:85–86, and Frishmen et al. (1992) *Fertility and Sterility* 58(3):630. When symptomatic treatment fails, pharmacological treatment may be indicated.

Estrogen therapy is commonly used in the pharmacological treatment of sexual dysfunction in women. Estrogen-based therapies are generally used to increase mucous production, provide vasodilatory effects, or to increase the general health of the vagina. Nadelson et al., eds., *Treatment Interventions in Human Sexuality* (New York: Plenum Press, 1983). In such treatments, estrogen is administered orally, parenterally (e.g., by injection), or topically. With oral administration, the estrogen concentration encountered by the liver is generally four- to five-fold greater than estrogen levels in peripheral blood (the "first pass effect"). This effect may lead to an undesirable increase in the production of certain coagulation factors and renin substrates by the liver. Parenterally administered estrogen avoids the first pass effect in the liver. However, all estrogen-based therapies are known to increase the risk of endometrial hyperplasia endometrial cancer and breast cancer in treated individuals.

Because of the increased risk of endometrial hyperplasia and endometrial cancer encountered with unopposed estrogen therapies, estrogen/progestogen combinations have been employed. However, progestogens are known to have some androgenic activity. Further, common side effects from such therapies include uterine bleeding and the continuation of menstrual periods. Accordingly, there remains a need in the art to provide safer and more ways of treating female sexual dysfunction.

The present invention is directed to the aforementioned need in the art, and provides a new, highly effective method of treating sexual dysfunction in women. The method involves vaginal, vulvar and/or urethral administration of a pharmaceutical formulation containing a vasoactive agent, e.g., a prostaglandin or the like.

Drug therapy for treating female sexual dysfunction has been described. For example, U.S. Pat. No. 4,507,323 to Stern describes the use of the anxiolytic m-chloro-α-t-butylamino-propiophenone in the treatment of sexual dysfunction in both male and female individuals. Pharmaceutical compositions containing the agent are described, which are presented in discrete units, e.g., cachets, tablets, capsules, ampules and suppositories, for oral or rectal delivery of the agent.

Additionally, U.S. Pat. No. 4,521,421 to Foreman describes the treatment of sexual dysfunction in male and female individuals using the stereoisomers of octahydropyrimido[4,5-g]quinolines, centrally acting dopamine agonists.

U.S. Pat. No. 5,190,967 to Riley describes the treatment of sexual disorders in male and female individuals using heterocyclic benzodioxinopyrrole compounds, which, like the drugs described in the aforementioned patents, are centrally acting agents.

U.S. Pat. No. 5,565,466 to Gioco et al., U.S. Pat. No. 5,731,339 to Lowrey, and U.S. Pat. No. 5,773,457 to Nahoum pertain to methods for modulating the human sexual response, with the Gioco et al. and Lowrey patents emphasizing the utility of phentolamine as an active agent.

A number of references describe various methods and devices suitable for vaginal or uterine drug administration, and may accordingly be of some interest with respect to the present invention. The following are representative of such references:

U.S. Pat. No. 3,967,618 to Zaffaroni describes an intrauterine device adapted for drug delivery. A number of drugs are mentioned as being suitable for use in conjunction with the device. However, the patent does not mention treatment of sexual dysfunction, nor is application of a drug-containing composition to the clitoris, vulvar area or urethra disclosed or suggested. U.S. Pat. No. 3,948,254 to Zaffaroni is a related patent that describes an intrauterine device for continuous administration of a contraceptive agent.

U.S. Pat. No. 4,014,987 to Heller et al. describes a tampon-like device for delivery of a drug to the uterus or vagina. Heller et al. mention that delivery of prostaglandins is a preferred use of the invention; however, there is no disclosure concerning treatment of sexual dysfunction or delivery to the vulvar area or urethra.

U.S. Pat. No. 4,564,362 to Burnhill describes a vaginal sponge for controlled release of a contraceptive agent.

U.S. Pat. No. 3,800,038 to Rudel describes a method and composition for uterine administration of steroid hormones. Prostaglandins such as $PGE_1$ are mentioned as useful in conjunction with the invention. However, there is no disclosure concerning vaginal drug delivery, urethral drug administration, application of a drug-containing formulation to the clitoris or surrounding vulvar area, or treatment of sexual dysfunction.

U.S. Pat. No. 4,961,931 to Wong describes a vaginal drug administration device adapted to deliver contraceptive hormones, including progestational and estrogenic hormones.

U.S. Pat. No. 4,112,942 to Scaife generally describes vaginal administration of medicinal foams.

The vaginal delivery of prostaglandins in connection with contraceptives, labor and delivery has also been described. U.S. Pat. No. 4,976,692 to Atad describes the uterine administration of a composition containing $PGF_2$ and triacetin gel in priming the cervix before induction of labor.

Vaginal $PGE_2$ suppositories ("Prostin E2®") and a cervical gel containing $PGE_2$ ("Prepidil"® gel), both manufactured by Upjohn (Kalamazoo, Mich.), are commercially available. See, e.g., Physicians' Desk Reference®, 51st Edition (Montvale, N.J.: Medical Economics Data Production Company, 1997). The suppositories are primarily indicated for evacuation of uterine contents, while the gel is used in connection with induction of labor.

U.S. Pat. No. 4,818,517 to Kwee et al., U.S. Pat. No. 4,680,312 to Johnson, U.S. Pat. No. 4,454,339 to Skuballa et al. and U.S. Pat. No. 4,128,577 to Nelson each relate to vaginal administration of prostaglandins. However, these patents focus on the use of prostaglandins in contraceptives, labor and delivery, and do not pertain to treatment of female sexual dysfunction.

U.S. Pat. No. 4,254,145 to Birnbaum relates to the use of prostaglandins, including natural and synthetic analogues of prostaglandin types PGE, PGA and $PGE_\beta$, in the treatment of arteriospastic and occlusive peripheral vascular disorders as well as in the treatment of impotency. The described methods of treatment involve topical administration or localized injection of pharmaceutical compositions containing the exemplified prostaglandins to increase peripheral circulation. The compositions are also described for use in lowering systemic blood pressure. Although a number of therapeutic applications are described, the patent does not suggest treatment of female sexual disorders using vaginal, vulvar or urethral delivery of prostaglandins.

Several references are also of interest herein insofar as they pertain to urethral drug administration to treat sexual dysfunction in men, e.g., vasculogenic impotence or the like. See, for example, U.S. Pat. Nos. 5,242,391, 5,474,535, 5,686,093 and 5,773,020 to Place et al. and U.S. Pat. No. 4,801,587 to Voss et al., which relate to the treatment of erectile dysfunction by delivery of a vasoactive agent into the male urethra.

There are, accordingly, a number of background references relating to treatment of female sexual dysfunction, cervical or uterine administration of prostaglandins, and urethral drug administration in men. However, the present method for treating female sexual dysfunction, by way of vaginal, vulvar and/or urethral delivery of a vasoactive agent such as a prostaglandin, is completely novel and unsuggested by the art.

SUMMARY OF THE INVENTION

Accordingly, it is a primary object of the invention to provide a method for treating sexual dysfunction in a female individual by administering a pharmaceutical formulation containing a selected vasoactive agent to the vagina, vulvar area or urethra of the individual undergoing treatment.

It is still another object of the invention to provide methods for preventing the occurrence of yeast infections, for improving vaginal muscle tone and tissue health, for enhancing vaginal lubrication, and for minimizing collagen misdeposition resulting from hypoxia, each of such methods involving vaginal, vulvar and/or urethral administration of a pharmaceutical formulation containing a selected vasoactive agent, in combination with a pharmaceutically acceptable vehicle.

It is a further object of the invention to provide pharmaceutical formulations useful in conjunction with the aforementioned methods.

It is still a further object of the invention to provide a drug delivery device for administering a pharmaceutical formulation directly to the clitoral area.

Additional objects, advantages and novel features of the invention will be set forth in part in the description that follows, and in part will become apparent to those skilled in the art upon examination of the following, or may be learned by practice of the invention.

In one aspect of the invention, then, a method is provided for treating sexual dysfunction in a female individual comprising administering to the vagina, vulvar area or urethra a pharmaceutical formulation containing a selected vasoactive agent. The vasoactive agent is preferably a vasodilator, with preferred vasodilators selected from the group consisting of naturally occurring prostaglandins, synthetic prostaglandin derivatives, endothelial-derived relaxation factors, vasoactive intestinal polypeptide agonists, smooth muscle relaxants, leukotriene inhibitors, pharmaceutically acceptable salts, esters, analogs, derivatives and inclusion complexes thereof, and combinations of any of the foregoing. Any number of drug delivery platforms may be used, e.g., suppositories, ointments, creams, gels, solutions and the like, which will be described in detail below. Also, one or more additional types of drugs, i.e., pharmacologically active agents other than vasoactive agents, may be incorporated into the pharmaceutical formulations. In other aspects of the invention, vaginal administration of a vasoactive agent as just described is used to prevent the occurrence of yeast infections, to improve vaginal muscle tone and tissue health, to enhance vaginal lubrication, or to minimize collagen misdeposition resulting from hypoxia as well as the associated lack of elasticity resulting from the collagen misdeposition.

In another aspect of the invention, pharmaceutical formulations are provided for carrying out the aforementioned methods. The formulations contain a vasoactive agent as described above, a pharmaceutically acceptable vehicle, and, optionally, one or more additional pharmacologically active agents.

In still another aspect of the invention, a drug delivery device is provided for administering a pharmaceutical formulation directly to the clitoral area. The device includes a drug reservoir comprising a vasoactive agent in a pharmaceutical formulation, as provided herein, and a clitoral applicator.

DETAILED DESCRIPTION OF THE INVENTION

Definitions

Before describing the present invention in detail, it is to be understood that this invention is not limited to delivery of specific drugs, carriers or use of particular drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a vasoactive agent" includes a mixture of two or more vasoactive agents, reference to "a pharmaceutically acceptable excipient" includes mixtures of such excipients, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic and/or physiologic effect by local and/or systemic action. The pharmacologically active agents used in conjunction with the present invention are vasoactive agents.

The term "vaginal delivery" is used herein to mean direct administration of a pharmaceutical composition to the vagina of the individual undergoing treatment. Generally, "vaginal delivery" of a pharmaceutical composition involves administration to the distal several centimeters of the vagina.

The term "vulvar delivery" or "vulvar administration" is used herein to refer to application of a pharmaceutical formulation to the vulvar area of an individual undergoing treatment. The term is intended to encompass application to the clitoris as well as the surrounding vulvar area. The terms "vulvar delivery" and "clitoral delivery" are used interchangeably herein and are both intended to refer to administration to the vulvar area of the individual undergoing treatment.

The term "urethral delivery" (sometimes referred to as "intraurethral" or "transurethral" delivery) is used herein to mean direct administration of a pharmaceutical composition to the urethra of the individual undergoing treatment. Generally, "urethral" delivery of a pharmaceutical composition involves administration to the distal portion of the urethra.

"Carriers" or "vehicles" as used herein refer to carrier materials suitable for vaginal, vulvar and/or urethral drug administration, and include any such materials known in the art, e.g., any liquid, gel, solvent, liquid diluent, solubilizer, or the like, which is nontoxic and which does not interact with other components present in the pharmaceutical formulation or drug delivery system in a deleterious manner.

By an "effective" amount of a drug or pharmacologically active agent is meant a nontoxic but sufficient amount of the drug or agent to provide the desired effect. For example, in treating sexual dysfunction in women, an "effective" amount of drug would be an amount that is at least sufficient to provide the desired degree of treatment. Similarly, in preventing yeast infections, an "effective" amount of drug would be an amount that is at least sufficient to prevent a vaginal yeast infection in a female individual.

In a first embodiment, the invention relates to a method for treating sexual dysfunction in a female individual and involves vaginal, vulvar and/or urethral administration of a pharmaceutical formulation containing a vasoactive agent, preferably a vasodilator. Preferred vasodilators are selected from the group consisting of naturally occurring prostaglandins, synthetic prostaglandin derivatives, endothelial-derived relaxation factors, vasoactive intestinal polypeptide agonists, smooth muscle relaxants, leukotriene inhibitors, pharmaceutically acceptable salts, esters, analogs, derivatives, prodrugs, and inclusion complexes thereof, and combinations of any of the foregoing, in combination with a pharmaceutically acceptable vehicle.

Particularly preferred vasodilating agents are naturally occurring prostaglandins or hydrolyzable lower alkyl esters of a naturally occurring prostaglandin, as well as synthetic or semisynthetic prostaglandins.

The "naturally occurring" prostaglandins useful in conjunction with the present invention are $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$ and $PGI_2$, with $PGE_0$, $PGE_1$ and $PGE_2$ particularly preferred. The term "synthetic prostaglandin derivatives" is intended to encompass known or unknown compounds related to the aforementioned naturally occurring prostaglandins that are chemically synthesized using starting materials other than one of the naturally occurring prostaglandins. The term "semisynthetic prostaglandin derivatives" refers to known or unknown compounds related to the aforementioned naturally occurring prostaglandins and that are synthesized therefrom. Synthetic and semisynthetic prostaglandins include, but are not limited to, carboprost tromethamine, dinoprost tromethamine, dinoprostone, lipoprost, gemeprost, metenoprost, sulprostone and tiaprost.

Additional vasoactive agents useful in conjunction with the present invention include endothelial-derived relaxation factors ("EDRFs") such as nitric oxide releasing agents, e.g., sodium nitroprusside and diazenium diolates, or "NONOates." NONOates include, but are not limited to, (Z)-1-{N-methyl-N-[6-(N-methyl-ammoniohexyl)amino]}diazen-1-ium-1,2-diolate ("MAHMA/NO"), (Z)-1-[N-(3-ammoniopropyl)-N-(n-propyl)amino]diazen-1-ium-1,2-diolate ("PAPA/NO"), (Z)-1-{N-[3-aminopropyl]-N-[4-(3-aminopropylammonio)butyl]amino}diazen-1-ium-1,2-diolate (spermine NONOate or "SPER/NO") and sodium (Z)-1-(N,N-diethylamino)-diazen-1-ium-1,2-diolate (diethylamine NONOate or "DEA/NO") and derivatives thereof). Still other vasoactive agents include vasoactive intestinal polypeptide agonists and derivatives thereof (particularly derivatives in the form of hydrolyzable lower alkyl esters), smooth muscle relaxants, leukotriene inhibitors, calcium channel blockers, β2-adrenergic agonists, angiotensin-converting enzyme ("ACE") inhibitors, and angiotensin II receptor antagonists, and phosphodiesterase inhibitors.

Suitable phosphodiesterase inhibitors include, but are not limited to, inhibitors of the type III phosphodiesterases (cAMP-specific-cGMP inhibitable form), the type IV phosphodiesterases (high affinity-high specificity cAMP form) and the type V phosphodiesterases (the cGMP specific form). Examples of type III phosphodiesterase inhibitors include, but are not limited to, bipyridines such as mihinone and amrinone, imidazolones such as piroximone and enoximone, dihydropyridazinones such as imazodan, 5-methylimazodan, indolidan and ICI118233 (6-(p-(3-methylureido)phenyl)-3(2H)-pyridazinone), quinolinone compounds such as cilostamide, cilostazol and vesnarinone, and other compounds such as bemoradan, anergrelide, siguazodan, trequensin, pimobendan, SKF-94120 (5-(4-acetamidophenyl)pyrazin-2-(1H)-one), SKF-95654, lixazinone and isomazole. Examples of type IV phosphodiesterase inhibitors include, but are not limited to, rolipram and rolipram derivatives such as RO20-1724 (4-(3-butyloxy-4-methoxyphenyl)-imidazolidinone), nitraquazone and nitraquazone derivatives such as CP-77059 (1-(carbomethoxyphenyl)-3-benzylpyrido[2,3d] pyrimidine-2, 4(1H,3H)dione), and RS-25344-00 (1-(3-nitrophenyl)-3-(4-pyridylmethyl)-1,2,3,4-tetrahydro pyrido(2,3-d) pyrimidine-2,4-dione)), xanthine derivatives such as denbufylline and ICI63197, and miscellaneous other compounds such as EMD54622 (5-[1-(3,4-dimethoxybenzoyl)-4,4-dimethyl-1, 2,3,4-tetrahydrochinolin-6-yl]-6-methyl-3,6-dihydro-1,3,4-thiadiazin-2-one), LAS-31025 (1-propyl-3-(4-chlorophenyl) xanthine; also referred to as arofylline) and etazolate.

Examples of type V phosphodiesterase inhibitors include, but are not limited to, zaprinast, MY5445 (N-(3-chlorophenyl)-4-phenyl-1-phthalazinamine), dipyridamole, and sildenafil. Sildenafil (5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one) and other suitable type V phosphodiesterase inhibitors are disclosed in PCT Publication Nos. WO 94/28902 and WO 96/16644.

The compounds described in PCT Publication No. WO 94/28902 are pyrazolopyrimidinones having the structural formula wherein:
$R^1$ is H, $C_1$–$C_3$ alkyl, $C_1$–$C_3$ perfluoroalkyl, or $C_3$–$C_5$ cycloalkyl;
$R^2$ is H; $C_1$–$C_6$ alkyl optionally substituted with $C_3$–$C_6$ cycloalkyl; $C_1$–$C_3$ perfluoroalkyl; or $C_3$–$C_6$ cycloalkyl;
$R^3$ is $C_1$–$C_6$ alkyl optionally substituted with $C_3$–$C_6$ cycloalkyl; $C_1$–$C_6$ perfluoroalkyl; $C_3$–$C_5$ cycloalkyl; $C_3$–$C_6$ alkenyl; or $C_3$–$C_6$ alkynyl;
$R_4$ is $C_1$–$C_4$ alkyl optionally substituted with OH, $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; (hydroxy)$C_2$–$C_4$ alkyl optionally substituted with $NR^5R^6$; ($C_2$–$C_3$ alkoxy)$C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^5$; $SO_2NR^9R^{10}$; or phenyl, pyridyl, pyrimidinyl, imidazolyl, oxazolyl, thiazolyl, thienyl or triazolyl any of which is optionally substituted with methyl;
$R^5$ and $R^6$ are each independently H or $C_1$–$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;
$R^7$ is H or $C_1$–$C_4$ alkyl;
$R^8$ is $C_1$–$C_3$ alkyl optionally substituted with $NR^5R^6$;
$R^9$ and $R^{10}$ together with the nitrogen atom to which they are attached form a pyrrolidinyl, piperidino, morpholino or 4-N($R^{12}$)-piperazinyl group wherein said group is optionally substituted with $C_1$–$C_4$ alkyl, $C_1$–$C_3$ alkoxy, $NR^{13}R^{14}$ or $CONR^{13}R^{14}$;
$R^{11}$ is H; $C_1$–$C_3$ alkyl optionally substituted with phenyl; (hydroxy)$C_2$–$C_3$ alkyl; or $C_1$–$C_4$ alkanoyl;
$R^{12}$ is H; $C_1$–$C_2$ alkyl; ($C_1$–$C_3$ alkoxy)$C_2$–$C_6$ alkyl; (hydroxy)$C_2$–$C_6$ alkyl; ($R^{13}R^{14}$N)$C_2$–$C_6$ alkyl; ($R^{13}R^{14}$NOC)$C_1$–$C_6$ alkyl; $CONR^{13}R^{14}$; $CSNR^{13}R^{14}$; or $C(NH)NR^{13}R^{14}$;
$R^{13}$ and $R^{14}$ are each independently H; $C_1$–$C_4$ alkyl; ($C_1$–$C_3$ alkoxy)$C_2$–$C_4$ alkyl; or (hydroxy)$C_2$–$C_4$ alkyl.

Examples of the inhibitor compounds include 5-(2-ethoxy-5-morpholinoacetyl-phenyl)-1-methyl-3-n-propyl-1, 6-dihydro-7H-pyrazolo[4,3-d]pyrimidin-7-one, 5-(5-morpholino-acetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d] pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl) phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d] pyrimidin-7-one, and 5-[2-ethoxy-5-(1-methyl-2-imidazolyl)phenyl]-1-methyl-3-n-propyl-1,6-dihydro-7H-pyrazolo[4,3-d]pyrimidin-7-one.

The phosphodiesterase inhibitors described in PCT Publication No. WO 96/16644 include griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidone derivative, imidazoquinoxalinone derivatives or aza analogues thereof, phenylpyridone derivatives, and others. More specifically, the inhibitor is
(i) a 5-substituted pyrazolo [4,3-d]pyrimidine-7-one as disclosed in European patent application 0201188;
(ii) a griseolic acid derivative as disclosed in European patent applications nos 0214708 and 0319050;
(iii) a 2-phenylpurinone derivative as disclosed in European patent application 0293063;
(iv) a phenylpyridone derivative as disclosed in European patent application 0347027;
(v) a fused pyrimidine derivative as disclosed in European patent application 0347146;
(vi) a condensed pyrimidine derivative as disclosed in European patent application 0349239;
(vii) a pyrimidopyrimidine derivative as disclosed in European patent application 0351058;

(viii) a purine compound as disclosed in European patent application 0352960;

(ix) a quinazolinone derivative as disclosed in European patent application 0371731;

(x) a phenylpyrimidone derivative as disclosed in European patent application 0395328;

(xi) an imidazoquinoxalinone derivative or its aza analogue as disclosed in European patent application 0400583;

(xii) a phenylpyrimidone derivative as disclosed in European patent application 0400799;

(xiii) a phenylpyridone derivative as disclosed in European patent application 0428268;

(xiv) a pyrimidopyrimidine derivative as disclosed in European patent 0442204;

(xv) a 4-aminoquinazoline derivative as disclosed in European patent application 0579496;

(xvi) a 4,5-dihydro-4-oxo-pyrrolo[1,2-a]quinoxaline derivative or its aza analogue as disclosed in European patent application 0584487;

(xvii) a polycyclic guanine derivative as disclosed in International patent application WO91/19717;

(xviii) a nitrogenous heterocyclic compound as disclosed in International patent application WO93/07124;

(xix) a 2-benzyl-polycyclic guanine derivative as disclosed in International patent application WO 94/19351;

(xx) a quinazoline derivative as disclosed in U.S. Pat. No. 4,060,615;

(xxi) a 6-heterocyclyl pyrazolo [3,4-d]pyrimidin-4-one as disclosed in U.S. Pat. No. 5,294,612;

(xxii) a benzimidazole as disclosed in Japanese patent application 5-222000;

(xxiii) a cycloheptimidazole as disclosed in European Journal of Pharmacology, 251, (1994), 1;

(xxiv) a N-containing heterocycle as disclosed in International patent application WO94/22855;

(xxv) a pyrazolopyrimidine derivative as disclosed in European patent application 0636626;

(xxvi) a 4-aminopyrimidine derivative as disclosed in European patent application 0640599;

(xxvii) a imidazoquinazoline derivative as disclosed in International patent application WO95/06648;

(xxviii) an anthranilic acid derivative as disclosed in International patent application WO95/18097;

(xxix) a 4-aminoquinazoline derivative as disclosed in U.S. Pat. No. 5,436,233;

(xxx) a tetracyclic derivative as disclosed in International patent application WO95/19978;

(xxxi) a imidazoquinazoline derivative as disclosed in European patent pplication 0668280; or (xxxii) a quinazoline compound as disclosed in European patent application 669324.

Specific examples of the phosphodiesterase inhibitors disclosed in WO 96/16644 include 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2(2-propoxyphenyl)-pyrimidine-4-carboxamide, 1-ethyl-3-methylimidazo[1,5a]quinoxalin-4(5H)-one, 4-phenyl-methylamino-6-chloro-2-(1-imidazoloyl)quinazoline, 5-ethyl-8-[3-(N-cyclohexyl-N-methyl-carbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]4'(5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a,7,8,9,9a-octahydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4,5-dihydro-1H-pyrazolo[3,4-d]pyrimid-4-one, 2-butyl-1-(2-chlorobenzyl)6-ethoxy-carbonylbenzimidaole, and 2-(4-carboxypiperidino)-4-(3,4-methylene-dioxybenzyl)amino-6-nitroquinazoline, and 2-phenyl-8-ethoxycycloheptimidazole.

Still other type V phosphodiesterase inhibitors useful in conjunction with the present invention include: IC-351 (ICOS), also referred to as tadalafil; 4-bromo-5-(pyridylmethylamino)-6-[3-(4-chlorophenyl)-propoxy]-3 (2H)pyridazinone; 1-[4-[(1,3-benzodioxol-5-ylmethyl) amiono]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]imidazo [2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)-propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl) amino]-6-chloro-2-quinazolinyl]-4-piperidinecarboxylic acid, monosodium salt; Pharmaprojects No. 4516 (Glaxo Wellcome), having the molecular structure Pharmaprojects No. 5051 (Bayer), having the molecular structure

Pharmaprojects No. 5064 (Kyowa Hakko; see WO 96/26940), having the molecular structure Pharmaprojects No. 5069 (Schering Plough), having the molecular structure and Sch-51866, having the molecular structure The pharmaceutical formulations of the invention include a vasoactive agent as just described, or a pharmaceutically acceptable salt, ester, analog, derivative, prodrug or inclusion complex thereof. Additionally, simultaneous administration of two or more vasoactive agents may be desirable and may in some cases exhibit a synergistic effect. The combination of prazosin with prostaglandin $E_1$ has been found to be particularly advantageous in this regard; the latter drug appears to act a permeation enhancer for prazosin, i.e., it appears to increase the rate at which prazosin permeates through the skin or mucosal tissue and enters the bloodstream.

"Pharmaceutically acceptable" salts, esters, analogs, derivatives, prodrugs or inclusion complexes refer to those salts, esters, analogs, derivatives, prodrugs and inclusion complexes that retain the biological effectiveness and properties of the base compounds and are not biologically or otherwise undesirable.

Salts, esters, analogs, derivatives, prodrugs and inclusion complexes of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). For example, acid addition salts are prepared from the free base (typically wherein the neutral form of the drug has a neutral —$NH_2$ group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on a drug are prepared in a similar manner using a pharmaceutically acceptable base such as sodium hydroxide, potassium hydroxide, ammonium hydroxide, calcium hydroxide, trimethylamine, or the like. For example, basic salts may be prepared from prostaglandins existing in acid form, i.e., prostaglandins retaining the prostanoic acid functionality, Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Inclusion complexes are complexes formed by interaction of macrocyclic compounds containing an intramolecular cavity of molecular dimensions with the smaller, pharmacologically active agent. Preferred inclusion complexes are formed from α-, β- and γ-cyclodextrins, or from clathrates, in which the "host" molecules form a crystal lattice containing spaces in which "guest" molecules (i.e., in this case, the vasoactive agent) will fit. See, e.g., Hagan, *Clathrate Inclusion Compounds* (New York: Reinhold, 1962). Inclusion complexes for use in conjunction with the method of the present invention can be prepared using methods known in the art, typically by admixing a macrocyclic compound such as a cyclodextrin with the active agent, under conditions that result in the incorporation of the active agent into the intramolecular cavity of the host molecule.

The pharmaceutical formulations used in the methods of the present invention may also include one or more pharmacologically active agents other than the vasoactive agent. For example, the formulations may contain a steroid or a steroid agonist, partial agonist, or antagonist.

Steroids will generally be selected from the group consisting of progestins, estrogens, and combinations thereof. Suitable progestins include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, cyproterone acetate, norethindrone, norethindrone acetate and levonorgestrel are preferred progestins. Suitable estrogens include synthetic and natural estrogens such as: estradiol (i.e., 1,3,5-estratriene-3,17β-diol, or "β-estradiol") and its esters, including estradiol benzoate, valerate, cypionate, heptanoate, decanoate, acetate and diacetate; 17β-estradiol; ethynylestradiol (i.e., 17β-ethynylestradiol) and esters and ethers thereof, including ethynylestradiol 3-acetate and ethynylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Estradiol and ethynylestradiol are particularly preferred.

Additionally, particularly for vulvar administration, it may be desirable to include an androgenic agent in the formulation. Suitable androgenic agents include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, ethylestrenol, oxandrolone, nandrolone phenpropionate, nandrolone decahoate, nandrolone furylpropionate, nandrolone cyclohexane-propionate, nandrolone benzoate, nandrolone cyclohexanecarboxylate, stanozolol, dromostanolone, dromostanolone propionate, testosterone, dehydroepiandrosterone (DHEA; also termed "prasterone"), sodium dehydroepiandrosterone sulfate, 4-dihydrotestosterone (DHT; also termed "stanolone"), and 5α-dihydrotestosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred.

Examples of preferred steroid antagonists or partial agonists are tamoxifen, cenchroman, clomiphene, droloxifene, raloxifene and pharmaceutically acceptable salts thereof, particularly tamoxifen or clomiphene citrate.

It may in some cases be desirable or necessary to include a detergent in the formulation, in an amount effective to increase solubility of the vasoactive agent in the vehicle and bioavailability of the agent following administration. The detergent will typically be a nonionic, anionic, cationic or amphoteric surfactant. In the practice of the invention, the surfactant is selected such that local irritation at the site of administration is avoided. Examples of suitable surfactants include Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), and pharmaceutically acceptable fatty acid esters such as lauryl sulfate and the like.

The formulations may also include a chemical compound to enhance permeation of the vasoactive agent through the mucosal tissue or urethral membrane, i.e., a "permeation enhancer." Suitable permeation enhancers include those generally useful in conjunction with topical, transdermal or transmucosal drug delivery. Examples of suitable permeation enhancers include dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), and surfactants as discussed above, including, for example, Tergitol®, Nonoxynol-9® and TWEEN-80®.

The pharmaceutical formulations used herein typically contain one or more pharmaceutically acceptable carriers (also termed "excipients" or "vehicles") suited to the particular type of formulation, i.e., gel, ointment, suppository, or the like. The vehicles are comprised of materials of naturally occurring or synthetic origin that do not adversely affect the vasoactive agent or other components of the formulation. Suitable carriers for use herein include water, silicone, waxes, petroleum jelly, polyethylene glycol, propylene glycol, liposomes, sugars such as mannitol and lactose, and a variety of other materials, depending, again, on the specific type of formulation used.

In some cases, the formulations used in the present methods include an enzyme inhibitor, i.e., a compound effective to inhibit enzymes present in the vagina, vulvar area or urethra that could degrade or metabolize the pharmacologically active agent. For example, with a prostaglandin as the active agent, it may be preferred to include an effective inhibiting amount of a compound effective to inhibit prostaglandin-degrading enzymes. Such compounds will include, for example, fatty acids, fatty acid esters, and NAD inhibitors. These formulations are believed to be novel.

The compositions used herein may be in the form of an ointment, cream, emulsion, lotion, gel, solid, solution, suspension, foam or Uposomal composition; such formulations may be used for clitoral, vulvar or vaginal delivery. Alternatively, the compositions may be contained within a vaginal ring, tampon, suppository, sponge, pillow, puff; or osmotic pump system; these platforms are useful solely for vaginal delivery. Preferred formulations for urethral delivery are ointments, emulsions, suppositories, liposomal compositions, powders, and the like. Preferred formulations are long-acting or pulsatile release solid phase systems, as well as ointments, gels and suppositories. Methods for preparing various dosage forms are known, or will be apparent, to those skilled in this art; for example, see *Remington's Pharmaceutical Sciences*, 18th Ed. (Easton, Pa.: Mack Publishing Company, 1990).

Ointments are semisolid preparations that are typically based on petrolatum or other petroleum derivatives. The specific ointment base to be used, as will be appreciated by those skilled in the art, is one that will provide for optimum drug delivery. As with other carriers or vehicles, an ointment base should be inert, stable, nonirritating and nonsensitizing. As explained in *Remington: The Science and Practice of Pharmacy*, supra, at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy* for further information.

Lotions are preparations that may be applied without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. It is generally necessary that the insoluble matter in a lotion be finely divided. Lotions will typically contain suspending agents to produce better dispersions as well as compounds useful for localizing the active agent in contact with the skin, e.g., methylcellulose, sodium carboxymethylcellulose, or the like.

Pharmaceutical emulsion formulations are generally formed from a dispersed phase (e.g., a pharmacologically active agent), a dispersion medium and an emulsifying agent. If desired, emulsion stabilizers can be included in the formulation as well. A number of pharmaceutically useful emulsions are known in the art, including oil-in-water (o/w) formulations, water-in-oil (w/o) formulations and multiple emulsions such as w/o/w or o/w/o formulations. Emulsifying agents suitable for use in such formulations include, but are not limited to, TWEEN 60®, Span 80®, cetostearyl alcohol, myristyl alcohol, glyceryl monostearate and sodium lauryl sulfate.

Pharmaceutical creams, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

The above pharmaceutical formulations are formed by dispersing the finely divided or dissolved vasoactive agent uniformly throughout the vehicle or base using conventional techniques, typically by a levigating the agent with a small quantity of the base to form a concentrate, which is then diluted geometrically with further base. Alternatively, a mechanical mixer may be used. Creams, lotions and emulsions are formed by way of a two-phase heat system, wherein oil-phase ingredients are combined under heat to provide a liquified, uniform system. The aqueous-phase ingredients are separately combined using heat. The oil and aqueous phases are then added together with constant agitation and allowed to cool. At this point, concentrated agents may be added as a slurry. Volatile or aromatic materials can be added after the emulsion has sufficiently cooled. Preparation of such pharmaceutical compositions is within the general skill of the art.

The vasoactive agent can also be incorporated into a gel formulation using known techniques. Two-phase gel systems generally comprise a suspension or network of small, discrete particles interpenetrated by a liquid to provide a dispersed phase and a liquid phase. Single-phase gel systems are formed by distributing organic macromolecules uniformly throughout a liquid such that there are no apparent boundaries between the dispersed and liquid phases. Suitable gelling agents for use herein include synthetic macromolecules (e.g., Carbomers®, polyvinyl alcohols and polyoxyethylene-polyoxypropylene copolymers), gums such as tragacanth, as well as sodium alginate, gelatin, methylcellulose, sodium carboxymethylcellulose, methylhydroxyethyl cellulose and hydroxyethyl cellulose. In order to prepare a uniform gel, dispersing agents such as alcohol or glycerin can be added, or the gelling agent can be dispersed by trituration, mechanical mixing or stirring, or combinations thereof.

Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1–2,3-dioleyloxy)propyl]-N,N,N-triethylammonium ("DOTMA") liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline ("DOPC"), dioleoylphosphatidyl glycerol ("DOPG"), dioleoylphoshatidyl ethanolamine ("DOPE"), among others. These materials can also be mixed with DOTMA in appropriate ratios. Methods for making liposomes using these materials are well known in the art.

The pharmaceutical formulations of the invention are typically contained within drug delivery systems that provide a specific, predetermined agent release profile, e.g., pulsatile, continuous, cyclical or diurnal. Such systems can include, for example, osmotic pumps that are capable of delivering variable amounts of the agent in a pulsatile manner. Osmotic pump systems typically involve incorporation of the pharmaceutical agent within a hard coating shell that is usually semi-permeable, e.g., a microporous cellulose acetate latex coating; the shell further contains a bore hole drilled into the outer layer. After delivery, water from the surrounding moist environment is osmotically pulled into shell through the bore hole, dissolving the agent and creating a high integral pressure sufficient to effect release of the agent from the shell. In this manner, the active agent is automatically "pulsed" out of the delivery system. A number of suitable osmotic pumps have been described in the art. See, for example, Appel et al. (1992) *Pharm. Res.* 9:1664–1667 and Kleinbloesem et al. (1984) *Clin. Pharm. Therapeut.* 36:396–401.

Other drug delivery platforms capable of providing a pulsatile, continuous, cyclical or diurnal agent release profile include those formed from bio-erodible polymers, wherein the vasoactive agent is dispersed within a polymer matrix. Such polymers are selected such that they bioerode in the presence of moisture, and provide for sustained agent release at readily predictable rates.

More particularly, release of the vasoactive agent can be controlled by dissolution (bioerosion) of a polymer using either encapsulated dissolution control or matrix dissolution control. In encapsulated dissolution control, the vasoactive agent is coated with a membrane of slowly dissolving polymeric or wax materials. When the encapsulating membrane has dissolved, the agent core is available for immediate release and adsorption across the epithelial or mucosal surfaces of the vagina or vulvar area. Bioerodible coating materials may be selected from a variety of natural and synthetic polymers, depending on the agent to be coated and the desired release characteristics. Exemplary coating materials include gelatins, carnauba wax, shellacs, ethylcellulose, cellulose acetate phthalate or cellulose acetate butyrate. Release of the agent is controlled by adjusting the thickness and dissolution rate of the polymeric membrane. A uniform sustained release formulation can be attained by compressing a population of particles of the agent with varying membrane thickness (e.g., varying erosion times) into a tablet form for a single administration.

In matrix dissolution control, the vasoactive agent is dissolved or dispersed within a matrix of, for example, an erodible wax. The agent is released for adsorption across the epithelial or mucosal surfaces of the vagina or vulvar area as the matrix bioerodes. The rate of agent availability is generally controlled by the rate of penetration of the dissolution media (i.e., vaginal fluids) into the matrix, wherein the rate of penetration is dependent on the porosity of the matrix material. Bioerodible matrix dissolution delivery systems can be prepared by compressing the vasoactive agent with a slowly soluble polymer carrier into a tablet or suppository form. There are several methods of preparing drug/wax particles including congealing and aqueous dispersion techniques. In congealing methods, the vasoactive agent is combined with a wax material and either spray-congealed, or congealed and then screened. For an aqueous dispersion, the vasoactive agent/wax combination is sprayed or placed in water and the resulting particles collected. Matrix dosage formulations can be formed by compaction or compression of a mixture of vasoactive agent, polymer and excipients.

In an alternative embodiment, the pharmaceutical formulation is administered in the form of biodegradable adhesive film or sheet that adheres to the vulvar area. Such drug delivery systems are generally composed of a biodegradable adhesive polymer based on a polyurethane, a poly(lactic acid), a poly(glycolic acid), a poly(ortho ester), a polyanhydride, a polyphosphazene, or a mixture or copolymer thereof. Preferred biodegradable adhesive polymers include polyurethanes and block copolyurethanes containing peptide linkages, simple mixtures of polyurethanes and polylactides, and copolymers of acrylates and mono- or disaccharide residues.

Figure 1:
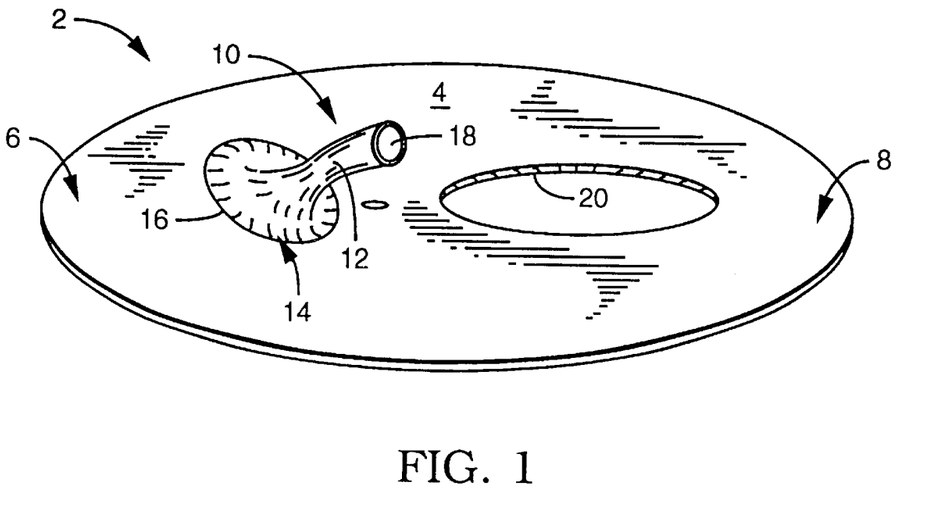
FIG. 1 is a pictorial representation of a clitoral drug application device that can be used as a carrier and dispenser for pharmaceutical compositions.

If desired, a clitoral application device may be used to facilitate application of a pharmaceutical formulation containing a vasoactive agent directly to the clitoral area. Referring to FIG. 1, an embodiment of a clitoral application device is generally indicated at 2. The device 2 is configured in the shape of an elongate patch having a top surface 4. The patch can be formed from any suitably flexible material such as polymers or fibrous materials. The patch is dimensioned to be generally co-extensive with the external female genitalia. The top surface 4 of the patch has an upper region 6 and a lower region 8 that correspond to the upper and lower portions of the female genitalia. A clitoral applicator, generally shown at 10, is provided on the top surface 4 of the patch at the upper region 6 thereof. The clitoral applicator 10 generally comprises an extended finger or protuberance 12 that is disposed over a reservoir 14 containing the pharmaceutical formulation. The reservoir 14 can be formed by disposing the pharmaceutical between the top surface 4 of the patch and a permeable membrane 16 that encircles the base of the protuberance 12. An optional suction tip 18 can be provided at the distal end of the protuberance 12 to facilitate positioning of the device.

The membrane 16 contains micropores through which the pharmaceutical agent can diffusively migrate to contact the clitoral wall. A number of suitable porous materials are known, such as water insoluble natural gums, cellulose, cellulose diacetate, microporous polyurethanes, polyarylenes, polycarbonates, polysulfones and polyamides, or microporous copolymers of polyvinylchloride and acrylonitrile. The release rate of the vasoactive agent can be readily controlled by adjusting the pore size in the membrane, the physical attributes of the pharmaceutical formulation (e.g., providing colloidal pharmaceutical solutions, suspensions or sols and/or adjusting the ratio of the size of the pores to the molecular size of the pharmaceutical agent), or by adjusting the thickness of the membrane. In addition, controlled or sustained release pharmaceutical formulations can be used in the application device 2 to provide a desired release effect.

In use, the device 2 is positioned by inserting the protuberance 12 to extend into the clitoral hood. The device can then be left in place for a suitable time to administer the vasoactive agent with the lower region 8 extending over the remainder of the genitalia. If desired, an opening 20 can be provided to allow for urethral voiding during drug administration. If the device includes a suction tip 18, a vacuum can be formed against the surface of the clitoral glans by pressing the protuberance firmly into place within the clitoris.

Transurethaal administration of the present formulations can be carried out in a number of different ways. For example, the drug can be introduced into the urethra from a flexible tube, squeeze bottle, pump or aerosol spray. The drug may also be contained in coatings, pellets or suppositories which are absorbed, melted or bioeroded in the urethra. The drug formulation may be included as a coating on the exterior surface of a urethral insert. A preferred drug delivery device for administering a drug transurethrally is shown in FIG. 2.

Figure 2:
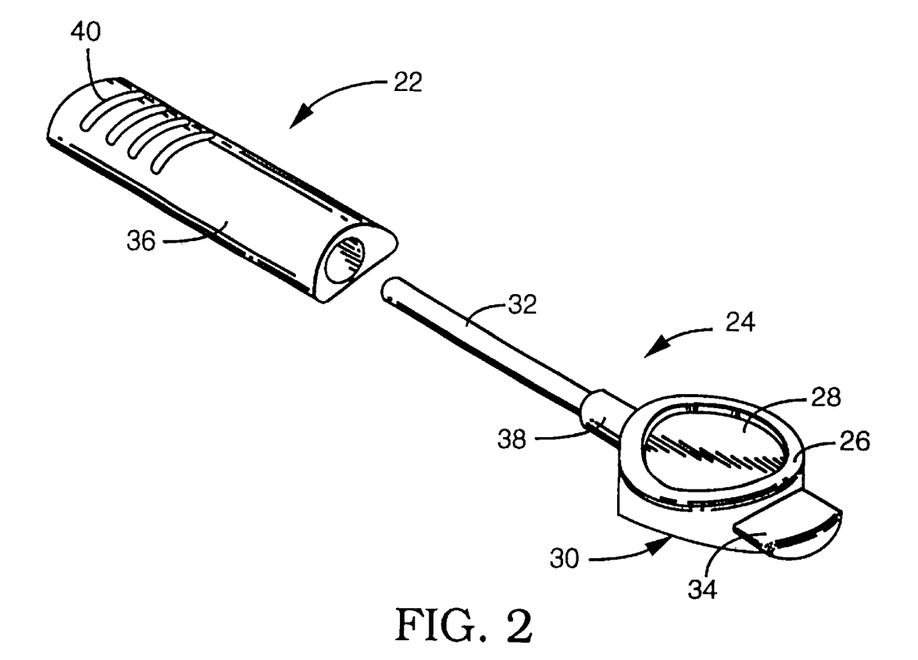
FIG. 2 is an exploded view of one embodiment of a transurethral therapeutic device which may be used in conjunction with the present method.

In FIG. 2, a transurethral drug delivery device is shown generally at 22. The device comprises a transurethral inserter 24 having an easily graspable segment 26 that has opposing symmetrically concave surfaces 28 and 30 adapted to be held by two fingers. Drug is contained within shaft 32, which is sized to fit within the urethra. A longitudinal plunger, the tip of which is seen at 34, is slidably insertable into the longitudinal bore contained within shaft 32. To extrude drug into the urethra, shaft 32 is inserted into the urethra, and plunger tip 34 is pushed into segment 26. The inserter 24 is then removed. Prior to use, and during storage, the device is capped with elongate cap 36 which fits snugly over flange 38 at the proximal end of shaft 32. The cap 36 is provided with a series of parallel ridges 40 to facilitate gripping of the cap and removal from inserter 24.

Although the configuration shown in FIG. 2 is a preferred configuration, other inserter/container configurations and mechanisms can be used, providing that a predetermined quantity of drug can be introduced from the inserter at a predetermined depth in the urethra For treatment of sexual dysfunction, the pharmaceutical formulation is administered either vaginally, to the vulvar area, and/or to the urethra The amount of active agent administered is at least the minimum necessary to treat the dysfunction, e.g., excitement stage dysfunctions such as touch sensation impairment, loss of clitoral sensation, vaginal dryness, urinary incontinence and concomitant dyspareunia. In the treatment of dyspareunia, prostaglandin $E_1$, $E_2$ and analogues thereof can be administered at a level sufficient to exceed naturally occurring levels at the point of administration, for example in an amount ranging from 50 to 500 µg/kg.

In addition to treatment of sexual dysfunction, the formulations of the invention have other uses as well. They may be administered vaginally to prevent the occurrence of yeast infections, to improve vaginal muscle tone and tissue health, to enhance vaginal lubrication, and to numinimize collagen misqeposition associated with hypoxia.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, patent publications and non-patent literature references mentioned herein are incorporated by reference in their entireties.

EXAMPLE 1

A cream formulation is prepared using a synthetic or semisynthetic prostaglandin. The cream includes the following components:

| Prostaglandin | 0.25 gm |
| Beeswax | 2.7 gm |
| Carbopol ® 934 q.s. | 100.0 gm |

Mixing is conducted with tile and spatula until a homogeneous cream mixture is obtained having the prostaglandin uniformly dispersed throughout the composition.

EXAMPLE 2

The procedure of Example 1 is repeated except that the following components are used:

| Prostaglandin | 0.25 gm |
| Polyethylene glycol 400 | 37.5 gm |
| 1, 2, 6-hexanetriol | 20.0 gm |
| Polyethylene glycol 4000 q.s. | 100.0 gm |

A homogenous cream mixture is obtained.

EXAMPLE 3

The procedure of Example 1 is repeated except that the following components are used:

| Prostaglandin | 0.25 gm |
| Polyethylene glycol 400 | 37.0 gm |
| Polyethylene glycol 400 monostearate | 26.0 gm |
| Polyethylene glycol 4000 q.s. | 100.0 gm |

A homogenous cream mixture is obtained.

EXAMPLE 4

The procedure of Example 1 is repeated except that the following components are used:

| Prostaglandin | 0.25 gm |
| Polyethylene glycol 400 | 47.5 gm |
| Cetyl Alcohol | 5.0 gm |
| Polyethylene glycol 4000 q.s. | 100.0 gm |

A homogenous cream mixture is obtained.

EXAMPLE 5

An ointment formulation is prepared using a synthetic or semisynthetic prostaglandin. The ointment includes the following components:

| Prostaglandin | 0.25 gm |
| Anhydrous lanolin | 20.0 gm |
| Mineral oil | 25.0 gm |
| White Petrolatum q.s. | 100.0 gm |

Mixing is conducted with tile and spatula until a homogeneous ointment mixture is obtained having the prostaglandin uniformly dispersed throughout the composition.

EXAMPLE 6

The procedure of Example 5 is repeated except that the following components are used:

| Prostaglandin | 0.25 gm |
| Diisopropyl Adipate | 19.95 gm |
| White Petrolatum, USP q.s. | 100.0 gm |

A homogenous ointment mixture is obtained.

In the cream and ointment formulations described in Examples 1–6, optional ingredients can include materials such as antioxidants, viscosity modifiers (e.g., paraffin wax or lanolin wax), and topical absorption rate modifiers. The formulations may be administered using the clitoral application device of FIG. 1.

EXAMPLE 7

A vaginal suppository formulation is prepared using a synthetic or semisynthetic prostaglandin. The suppository includes the following components:

| Prostaglandin | 0.25 gm |
| Polyethylene glycol 400 | 37.0 gm |
| Glycerol gelatin | 20.0 gm |
| Polyethylene glycol 4000 q.s. | 100.0 gm |

The polyethylene glycol 400 solution containing prostaglandin is mixed well with glycerol gelatin or similar suppository base such as macrogol, Witepsol®, or the like, with a mechanical mixing apparatus, and the mixture is then cooled in a suppository mold.

EXAMPLE 8

Suppositories suitable for transurethral administration of a unit dosage of synthetic or semisynthetic prostaglandin are prepared. A pharmaceutical formulation containing a prostaglandin for transurethral administration is prepared by mixing the selected prostaglandin with polyethylene glycol, molecular weight ($M_w$) approximately 4000, and heating the mixture to a temperature just high enough to produce a prostaglandin-polymer melt. The prostaglandin-glycol mixture can then be poured into a mold suitable to provide a prostaglandin suppository, and allowed to cool. The suppository so provided is a unit dosage form suitable for transurethia administration. If desired, the prostaglandin-glycol mixture may be allowed to cool on the tip of a rod adapted to be inserted into the urethra.

EXAMPLE 9

The procedure of Example 8 is repeated, except that cocoa butter is substituted for polyethylene glycol.

EXAMPLE 10

A prostaglandin-pharmaceutical formulation containing prostaglandin for transurethral administration is prepared by dissolving a prostaglandin in a sufficient quantity of water. Glycerin (70%) is then added, followed by addition of Pharmagel A or B (20%). Suppositories are then prepared as described in Example 8.

EXAMPLE 11

Individuals are assessed and pre-screened to assemble an experimental group of subjects suffering from sexual dysfunction. The compositions prepared in Examples 1–6, formulated with prostaglandin $E_1$, each assessed in the experimental subjects for their ability to increase uterine or vaginal epithelial blood flow. The formulations are applied vaginally, and changes in blood flow or vaginal fluid production after application of the vasodilating formulations are determined using known methods. Increase in vaginal epithelial blood flow is determined using indirect methods such as photoplethysmography (Levin (1980) *Clinics in Obstet. Gynaecol.* 7:213–252), heated oxygen electrode (Wagner et al. (1978), "Vaginal Fluid" in *The Human Vagina*, Evans et al. (eds.), Amsterdam: Elsevier/North Holland Biomedical Press, pp. 121–137), and direct clearance of radioactive Xenon (Wagner et al. (1980) *Obstet. Gynaecol.* 56:621–624). Changes in vulvar blood flow are monitored using laser Doppler velocimetry (Sarrel, P. M. (1990) *Obstet. Gynaecol.* 75:26S–32S).

Decreased vaginal dryness and/or dyspareunia are negatively correlated with vaginal blood flow rates, wherein increased blood flow to the vagina correlates with increased lubrication and decreased frequency and severity of dyspareunia (Sarrel, P. M. (1990) *Obstet. Gynaecol.* 75:26S–32S). Accordingly, vulvar blood flow after treatment is assessed using laser Doppler velocimetry and compared to baseline levels. Increased vaginal lubrication as a result of treatment with the vasoactive formulations can also be assessed using the methods of Semmens et al. (1982) *J. Am. Med. Assoc.* 248:445–448. The compositions of Examples 1–6, when assessed using such methods, are found to substantially increase blood flow to the vagina and vulvar area and alleviate vaginal dryness.

EXAMPLE 12

The method of Example 11 is repeated using the suppository formulation of Example 7. Substantially the same results are obtained.

EXAMPLE 13

The method of Example 11 is repeated, but the formulations are applied topically, to the vulvar area, instead of vaginally. Substantially the same results are obtained.

EXAMPLE 14

The method of Example 11 is repeated using the urethral suppositories of Examples 8, 9 and 10, and the compositions are administered transurethrally instead of vaginally. Substantially the same results are obtained.

What is claimed is:

1. A method for treating sexual dysfunction in a female individual, comprising administering to the vagina and/or vulvar area of the individual a pharmaceutical formulation that comprises an effective amount of a vasoactive agent selected from the group consisting of a Type V phosphodiesterase inhibitor, pharmaceutically acceptable salts, esters, analogs, derivatives, prodrugs and inclusion complexes thereof, and combinations of any of the foregoing.

2. The method of claim 1, wherein the pharmaceutical formulation further includes a pharmaceutically acceptable carrier suited to vaginal and/or vulvar drug administration.

3. The method of claim 1, wherein the pharmaceutical formulation is contained within a delivery system that provides a predetermined agent release profile.

4. The method of claim 3, wherein the agent release profile is pulsatile.

5. The method of claim 3, wherein the agent release profile is continuous.

6. The method of claim 3, wherein the agent release profile is cyclical.

7. The method of claim 3, wherein the agent release profile is diurnal.

8. The method of claim 1, wherein the pharmaceutical formulation is administered vaginally.

9. The method of claim 8, wherein the pharmaceutical formulation is in the form of an ointment, cream, gel, solid, solution, suspension, foam or liposomal composition.

10. The method of claim 8, wherein the pharmaceutical formulation is contained within a vaginal ring, tampon, suppository, sponge, pillow, puff, or osmotic pump system.

11. The method of claim 1, wherein the pharmaceutical formulation is administered to the vulvar area of the individual.

12. The method of claim 8, wherein the method further comprises co-administering an androgenic agent to the vulvar area of the individual in combination with vaginal administration of the vasoactive agent.

13. The method of claim 12, wherein the androgenic agent is testosterone or a testosterone ester.

14. The method of claim 1, wherein the sexual dysfunction is an excitement stage dysfunction.

15. The method of claim 14, wherein the sexual dysfunction involves touch sensation impairment, loss of clitoral sensation, dyspareunia, or a combination thereof.

16. The method of claim 1, wherein the sexual dysfunction involves dyspareunia.

17. The method of claim 1, wherein the vasoactive agent is selected from the group consisting of a Type V phosphodiesterase inhibitor and pharmaceutically acceptable salts thereof.

18. The method of claim 17, wherein the Type V phosphodiesterase inhibitor is selected from the group consisting of zaprinast, N-(3-chlorophenyl)-4-phenyl-1-phthalazinamine (MY5445), dipyridamole, pyrazolopyrimidinones, griseolic acid derivatives, 2-phenlypurinones, phenylpyridone derivatives, pyrimidines, pyrimidopyrimidines, purines, quinazolines, quinazolinones, quinoxalines, benzimidazoles, cycloheptimidazoles, phenylpyrimidinones, imidazoquinazolines, and imidazoquinoxalinones or aza analogues thereof.

19. The method of claim 18, wherein the Type V phosphodiesterase inhibitor is zaprinast.

20. The method of claim 18, wherein the Type V phosphodiesterase inhibitor is a pyrazolopyrimidinione.

21. The method of claim 20, wherein the pyrazolopyrimidinone has the structural formula wherein:
R¹ is H, $C_1$–$C_3$ alkyl, $C_1$–$C_3$ perfluoroalkyl, or $C_3$–$C_5$ cycloalkyl;
R² is H; $C_1$–$C_6$ alkyl optionally substituted with $C_3$–$C_6$ cycloalkyl; $C_1$–$C_3$ perfluoroalkyl; or $C_3$–$C_6$ cycloalkyl;
R³ is $C_1$–$C_6$ alkyl optionally substituted with $C_3$–$C_6$ cycloalkyl; $C_1$–$C_6$ perfluoroalkyl; $C_3$–$C_5$ cycloalkyl; $C_3$–$C_6$ alkenyl; or $C_3$–$C_6$ alkynyl;
R⁴ is $C_1$–$C_4$ alkyl optionally substituted with OH, $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; (hydroxy)$C_2$–$C_4$ alkyl optionally substituted with $NR^5R^6$; ($C_2$–$C_3$ alkoxy)$C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl;
R⁵ and R⁶ are each independently H or $C_1$–$C_4$ alkyl, or together with the nitrogen atom to which they are attached form a pyrrolidinyl, piperidino, morpholino, 4-N($R^{11}$)-piperazinyl or imidazolyl group wherein said group is optionally substituted with methyl or OH;
R⁷ is H or $C_1$–$C_4$ alkyl;
R⁸ is $C_1$–$C_3$ alkyl optionally substituted with $NR^5R^6$;
R⁹ and R¹⁰ together with the nitrogen atom to which they are attached form a pyrrolidinyl, piperidino, morpholino or 4-N($R^{12}$)-piperazinyl group wherein said group is optionally substituted with $C_1$–$C_4$ alkyl, $C_1$–$C_3$ alkoxy, $NR^{13}R^{14}$ or $CONR^{13}R^{14}$; R¹¹ is H; $C_1$–$C_3$ alkyl optionally substituted with phenyl; (hydroxy)$C_2$–$C_3$ alkyl; or $C_1$–$C_4$ alkanoyl;
R¹² is H; $C_1$–$C_2$ alkyl; ($C_1$–$C_3$ alkoxy)$C_2$–$C_6$ alkyl; (hydroxy)$C_2$–$C_6$ alkyl; ($R^{13}R^{14}N$)$C_2$–$C_6$ alkyl; ($R^{13}R^{14}NOC$)$C_1$–$C_6$ alkyl; $CONR^{13}R^{14}$; $CSNR^{13}R^{14}$; or $C(NH)NR^{13}R^{14}$;
R¹³ and R¹⁴ are each independently H; $C_1$–$C_4$ alkyl; ($C_1$–$C_3$ alkoxy)$C_2$–$C_4$ alkyl; or (hydroxy)$C_2$–$C_4$ alkyl.

22. The method of claim 21, wherein the pyrazolopyrimidinone is selected from the group consisting of 5-(2-ethoxy-5-morpholinoacetylphenyl)-1-methyl-3-n-propyl-1,6-dihydro-7H-pyrazolo[4,3-d]pyrimidin-7-one, 5-(5-morpholino-acetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonylphenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one, and 5-[2-ethoxy-5-(1-methyl-2-imidazolyl)phenyl]-1-methyl-3n-propyl-1,6-dihydro-7H-pyrazolo[4,3-d]pyrimidin-7-one.

23. The method of claim 22, wherein the pyrazolopyrimidinone is 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one.

24. The method of claim 18, wherein the Type V phosphodiesterase inhibitor is selected from the group consisting of 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl)-pyrimidine-4-carboxamide, 1-ethyl-3-methylimidazo[1,5a]quinoxalin-4(5H)-one, 4-phenylmethylamino-6-chloro-2-(1-imidazoloyl)quinazoline, 5-ethyl-8-[3-(N-cyclohexyl-N-methyl-carbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]4'(5'H)-one, 1-[6-chloro-4-(3,4methylenedioxybenzyl)-aminoquinazolin-2-yl)piperidine-4-carboxylic acid, (6R, 9S)-2-(4-trifluoromethyl-phenyl)methyl-5-methyl-3,4,5,6a,7,8,9,9a-octahydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4,5-dihydro-1H-pyrazolo[3,4-d]pyrimid-4-one, 2-butyl-1-(2-chlorobenzyl)6-ethoxy-carbonylbenzimidaole, and 2-(4-caraboxypiperidino)-4-(3,4-methylene-dioxybenzyl)amino-6-nitroquinazoline, and 2-phenyl-8-ethoxycycloheptimidazole.

25. The method of claim 18, wherein the Type V phosphodiesterase inhibitor is tadalafil.

26. The method of claim 1, wherein the pharmaceutical formulation further includes a steroid.

27. The method of claim 26, wherein the steroid is selected from the group consisting of progestins, estrogens and mixtures thereof.

28. The method of claim 1, wherein the pharmaceutical formulation further includes a compound selected from the group consisting of steroid agonists, partial agonists and antagonists.

29. The method of claim 28, wherein the compound is selected from the group consisting of steroid agonists and partial agonists.

30. The method of claim 28, wherein the compound is selected from the group consisting of tamoxifen, cenchroman, cloriphene, droloxifene, raloxifene and pharmaceutically acceptable salts thereof.

31. The method of claim 2, wherein the pharmaceutical formulation additionally includes a detergent in an amount effective to increase the solubility of the vasoactive agent in the carrier and the bioavailability of the agent following administration.

32. A method for improving vaginal muscle tone and tissue health in a female individual, comprising vaginally administering to such individual a pharmaceutical formulation that comprises a vasoactive agent selected from the group consisting of a Type V phosphodiesterase inhibitor, pharmaceutically acceptable salts, esters, analogs, derivatives, prodrugs and inclusion complexes thereof, and combinations of any of the foregoing, in combination with a pharmaceutically acceptable carrier.

33. The method of claim 32, wherein the vasoactive agent is selected from the group consisting of a Type V phosphodiesterase inhibitor and pharmaceutically acceptable salts thereof.

34. A method for enhancing vaginal lubrication in a female individual, comprising vaginally administering to such individual a pharmaceutical formulation that comprises a vasoactive agent selected from the group consisting of a Type V phosphodiesterase inhibitor, pharmaceutically acceptable salts, esters, analogs, derivatives, prodrugs and inclusion complexes thereof, and combinations of any of the foregoing, in combination with a pharmaceutically acceptable carrier.

35. The method of claim 34, wherein the vasoactive agent is selected from the group consisting of a Type V phosphodiesterase inhibitor and pharmaceutically acceptable salts thereof.

36. A method for treating sexual dysfunction in a female individual, comprising administering to the vagina and/or vulvar area of the individual (a) a therapeutically effective amount of a Type V phosphodiesterase inhibitor or a pharmaceutically acceptable salt or ester thereof, and (b) a therapeutically effective amount of an additional active agent selected from the group consisting of additional vasodilators, androgenic agents, and combinations thereof.

37. The method of claim 36, wherein the additional active agent is an additional vasodilator.

38. The method of claim 37, wherein the additional vasodilator is selected from the group consisting of prostaglandins, endothelial-derived relaxation factors, vasoactive intestinal polypeptide agonists, smooth muscle relaxants, leukotriene inhibitors, and combinations thereof.

39. The method of claim 38, wherein the additional vasodilator is a prostaglanidin.

40. The method of claim 39, wherein the prostaglandin is $PGE_0$, $PGE_1$, $PGE_2$, or a combination thereof.

41. The method of claim 40, wherein the prostaglandin is $PGE_1$.

42. The method of claim 37, wherein the additional vasodilator is a nitrovasodilater.

43. The method of claim 36, wherein the additional active agent is an androgenic agent.

44. The method of claim 43, wherein the androgenic agent is selected from the group consisting of androsterone, androsterone acetate, androsterone, androstenediol, androstenedione, ethylestrenol, oxandrolone, nandrolone, stanozolol, dromostanolone, testosterone, dehydroepiandrosterone, 5α-dihydrotestosterone, methyl testosterone, testolactone, oxymetholone, fluoxymesterone, and pharmaceutically acceptable esters thereof.

45. The method of claim 37, wherein the androgenic agent is selected from the group consisting of testosterone, 5α-dihydrotestosterone, and pharmaceutically acceptable esters thereof.

46. The method of claim 45, wherein the androgenic agent is testosterone.

47. The method of claim 45, wherein the androgenic agent is 5α-dihydrotestosterone.

48. The method of claim 45, wherein the androgenic agent is a testosterone ester.

49. The method of claim 48, wherein the testosterone ester is selected from the group consisting of testosterone enanthate, testosterone propionate, testosterone cypionate, testosterone phenylacetate, testosterone acetate, testosterone isobutyrate, testosterone buciclate, testosterone heptanoate, testosterone decanoate, testosterone undecanoate, testosterone caprate and testosterone isocaprate.

50. The method of claim 49, wherein the testosterone ester is testosterone propionate.

51. The method of claim 45, wherein the androgenic agent is a 5α-dihydrotestoserone ester.

52. The method of claim 51, wherein the 5α-dihydrotestosterone ester is selected from the group consisting of the 5α-dihydrotestosterone enanthate, 5α-dihydrotestosterone propionate, 5α-dihydrotestosterone cypionate, 5α-dihydrotestosterone phenylacetate, 5α-dihydrotestosterone acetate, 5α-dihydrotestosterone isobutyrate, 5α-dihydrotestosterone buciclate, 5α-dihydrotestosterone heptanoate, 5α-dihydrotestosterone decanoate, 5α-dihydrotestosterone undecanoate, 5α-dihydrotestosterone caprate and 5α-dihydrotestosterone isocaprate.

53. The method of claim 36, wherein the sexual dysfunction is an excitement stage dysfunction.

54. The method of claim 53, wherein the sexual dysfunction involves touch sensation impairment, loss of clitoral sensation, dyspareunia, or a combination thereof.

55. The method of claim 36, wherein the sexual dysfunction involves dyspareunia.

56. The method of claim 36, wherein the Type V phosphodiesterase inhibitor is selected from the group consisting of zaprinast, N-(3-chlorophenyl)-4-phenyl-1-phthalazinamine (MY5445), dipyridamole, pyrazolopyrimidinones, griseolic acid derivatives, 2-phenylpurinones, phenylpyridone derivatives, pyrimidines, pyrimidopyrimidines, purines, quinazolines, quinazolinones, quinoxalines, benzimidazoles, cycloheptimidazoles, phenylpyrimidinones, imidazoquinazolines, and imidazoquinoxalinones or aza analogues thereof.

57. The method of claim 36, wherein the vasoactive agent is selected from the group consisting of a Type V phosphodiesterase inhibitor and pharmaceutically acceptable salts thereof.

58. The method of claim 57, wherein the Type V phosphodiesterase inhibitor is zaprinast.

59. The method of claim 57, wherein the Type V phosphodiesterase inhibitor is a pyrazolopyrimidinone.

60. The method of claim 59, wherein the pyrazolopyrimidinone has the structural formula having the structural formula wherein:
$R^1$ is H, $C_1$–$C_3$ alkyl, $C_1$–$C_3$ perfluoroalkyl, or $C_3$–$C_5$ cycloalkyl;
$R^2$ is H; $C_1$–$C_6$ alkyl optionally substituted with $C_3$–$C_6$ cycloalkyl; $C_{1-3}$ perfluoroalkyl; or $C_3$–$C_6$ cycloalkyl;
$R^3$ is $C_1$–$C_6$ alkyl optionally substituted with $C_3$–$C_6$ cycloalkyl; $C_1$–$C_6$ perfluoroalkyl; $C_3$–$C_5$ cycloalkyl; $C_3$–$C_6$ alkenyl; or $C_3$–$C_6$ alkynyl;
$R^4$ is $C_1$–$C_4$ alkyl optionally substituted with OH, $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; (hydroxy)$C_2$–$C_4$ alkyl optionally substituted with $NR^5R^6$; ($C_2$–$C_3$ alkoxy)$C_1$–$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; $SO_2NR^9R^{10}$; or phenyl, pyridyl, pyrimidinyl, imidazolyl, oxazolyl, thiazolyl, thienyl or triazolyl any of which is optionally substituted with methyl;
$R^5$ and $R^6$ are each independently H or $C_1$–$C_4$ alkyl, or together with the nitrogen atom to which they are attached form a pyrrolidinyl, piperidino, morpholino, 4-N(R$^{11}$)-piperazinyl or imidazolyl group wherein said group is optionally substituted with methyl or OH;

R$^7$ is H or C$_1$–C$_4$ alkyl;

R$^8$ is C$_1$–C$_3$ alkyl optionally substituted with NR$^5$R$^6$;

R$^9$ and R$^{10}$ together with the nitrogen atom to which they are attached form a pyrrolidinyl, piperidino, morpholino or 4-N(R$^{12}$)-piperazinyl group wherein said group is optionally substituted with C$_1$–C$_4$ alkyl, C$_1$–C$_3$ alkoxy, NR$^{13}$R$^{14}$ or CONR$^{13}$R$^{14}$; R$^{11}$ is H; C$_1$–$_3$ alkyl optionally substituted with phenyl; (hydroxy)C$_2$–C$_3$ alkyl; or C$_1$–C$_4$ alkanoyl;

R$^{12}$ is H; C$_1$–C$_2$ alkyl; (C$_1$–C$_3$ alkoxy)C$_2$–C$_6$ alkyl; (hydroxy)C$_2$–C$_6$ alkyl; (R$^{13}$R$^{14}$N)C$_2$–C$_6$ alkyl; (R$^{13}$R$^{14}$NOC)C$_1$–C$_6$ alkyl; CONR$^{13}$R$^{14}$; CSNR$^{13}$R$^{14}$; or C(NH)NR$^{13}$R$^{14}$;

R$^{13}$ and R$^{14}$ are each independently H; C$_1$–C$_4$ alkyl; (C$_1$–C$_3$ alkoxy)C$_2$–C$_4$ alkyl; or (hydroxy)C$_2$–C$_4$ alkyl.

61. The method of claim 60, wherein the pyrazolopyrimidinone is selected from the group consisting of 5-(2-ethoxy-5-morpholinoacetylphenyl)-1-methyl-3-n-propyl-1,6-dihydro-7H-pyrazolo[4,3-d]pyrimidin-7-one, 5-(5-morpholino-acetyl-2-n-propoxyphenyl)-1-methyl-3-n-propyl-1.6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl)phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl-3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one, and 5-[2-ethoxy-5-(1-methyl-2imidazolyl)phenyl]-1-methyl-3-n-propyl-1,6-dihydro-7H-pyrazolo[4,3-d]pyrimidin-7one.

62. The method of claim 61, wherein the pyrazolopyrimidinone is 5-(4-methyl-1-piperazinylsulfonyl)-phenyl]-1-methyl-3-n-propyl-1,6-dihydro-7H-pyrazolo[4,3-d]pyrimidin-7one.

63. The method of claim 57, wherein the Type V phosphodiesterase inhibitor is selected from the group consisting of 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl)-pyrimidine-4-carboxamide, 1-ethyl-3-methyl-imidazo[1,5a]quinoxalin-4(5H)-one, 4-phenyl-methylamino-6-chloro-2-(1-imidazoyloyl)quinazoline, 5-ethyl-8-[3-(N-cyclohexyl-N-methyl-carbamoyl)-propyloxy]-4,5-dihydro-4-oxo-pyrido-3,2-c]-pyrrolo[1,2-a]pyrazine, 5'-methyl-3'-(phenylmethyl)-spiro[cyclopentane-1,7'(8'H)-(3'H)-imidazo[2,1-b]purin]4'(5'H)-one, 1-[6-chloro-4-(3,4-methylenedioxybenzyl)-aminoquinazolin-2-yl)piperidine-4-carboxylic acid, (6R,9S)-2-(4-trifluoromethyl-phenyl)methyl-5-methyl-3,4,5,6a,7,8,9,9a,-octahydrocyclopent[4,5]-imidazo[2,1-b]-purin-4-one, 1-t-butyl-3-phenylmethyl-6-(4-pyridyl)pyrazolo[3,4-d]-pyrimid-4one, 1-cyclopentyl-3-methyl-6-(4-pyridyl)-4,5-dihydro-1H-pyrazolo[3,4d]pyrimid-4-one, 2-butyl-1-(2-chlorobenzyl)6-ethoxy-carbonylbenzimidaole, and 2-(4-carboxypiperidino)-4-(3,4-methylene-dioxybenzyl)amino-6-nitroquinazoline, and 2-phenyl-8-ethoxycycloheptimidazole.

64. The method of claim 57, wherein the Type V phosphodiesterase inhibitor is tadalafil.

\* \* \* \* \*